United States Patent [19]

Tam

[11] Patent Number: 4,866,614
[45] Date of Patent: Sep. 12, 1989

[54] ULTRASOUND CHARACTERIZATION OF 3-DIMENSIONAL FLAWS

[75] Inventor: Kwok C. Tam, Schenectady, N.Y.

[73] Assignee: General Electric Company, Schenectady, N.Y.

[21] Appl. No.: 231,932

[22] Filed: Aug. 15, 1988

Related U.S. Application Data

[63] Continuation of Ser. No. 813,455, Dec. 26, 1985, abandoned.

[51] Int. Cl.$^4$ ............... G06F 15/42; G01N 29/04
[52] U.S. Cl. .................... 364/413.25; 364/507; 364/551.01; 128/660.01; 128/660.07; 128/660.06; 73/600; 73/602
[58] Field of Search ............... 364/507, 550, 551.01, 364/413.13, 413.14, 413.15, 413.19, 413.2, 413.22, 413.25; 73/598, 600, 602, 607, 613; 324/456; 128/660.06, 660.07, 660.8, 661.03, 660.01, 660.04

[56] References Cited

U.S. PATENT DOCUMENTS

| | | | |
|---|---|---|---|
| 4,210,904 | 7/1980 | Renzel et al. | 364/507 |
| 4,282,577 | 8/1981 | Abend et al. | 364/507 |
| 4,372,163 | 2/1983 | Tittman et al. | 73/602 |
| 4,475,394 | 10/1984 | Takeda et al. | 73/602 |
| 4,506,327 | 3/1985 | Tam | 364/414 |
| 4,594,662 | 6/1986 | Devaney | 73/602 |
| 4,598,366 | 7/1986 | Devaney | 364/421 |
| 4,662,222 | 5/1987 | Johnson | 73/607 |
| 4,665,228 | 4/1987 | Shimura et al. | 73/602 |
| 4,682,296 | 7/1987 | Parker | 73/602 |
| 4,805,627 | 2/1989 | Klingenbeck | 73/602 |

OTHER PUBLICATIONS

Rose et al., "Determination of Flaw Characteristics for Ultrasonic Scattering Data", J. Appl. Phys., 50(4), Apr. 1979, pp. 2951-2952.
Rose et al., "Inversion of Ultrasonic Scattering Data", Acoustic, Electromagnetic & Elastic Wave Scattering, 1980, pp. 605-614.
Tam et al., "Tomographical Imaging with Limited-Angle Input", J. Opt. Soc. Am. 71, May 1981, pp. 582-592.

Primary Examiner—Parshotam S. Lall
Assistant Examiner—Brian M. Mattson
Attorney, Agent, or Firm—Donald R. Campbell; James C. Davis, Jr.; Paul R. Webb, II

[57] ABSTRACT

This ultrasound inspection method using the Born approximation simplifies the problem of characterizing 3-dimensional flaws of general shape by reducing it to a series of 2-dimensional tomographic image reconstructions. The reconstructed 2-dimensional images represent the 2-dimensional projections or shadows of the 3-dimensional flaw characteristic function which specifies the shape of the flaw. Each projection image is reconstructed independently using well developed computerized tomography techniques. If the shape of the flow is not too irregular or fine details are not of interest, only a few of these projection images are needed. The 3-dimensional flaw shape is reconstructed from the 2-dimensional projection images through a 3-D reconstruction process.

4 Claims, 5 Drawing Sheets

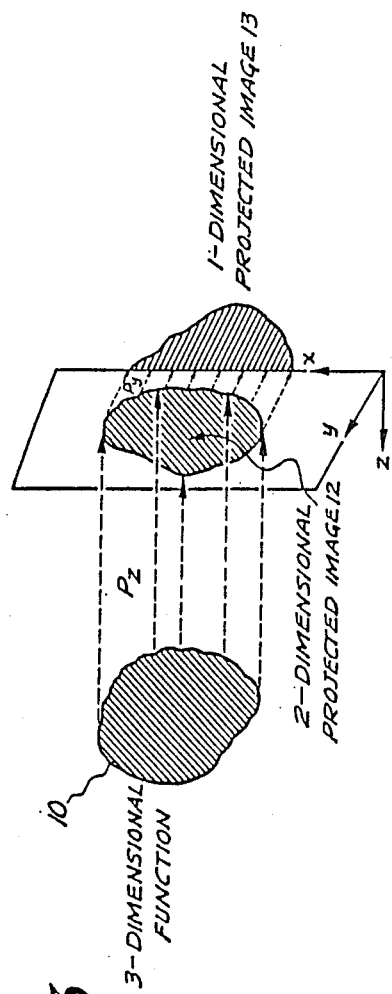
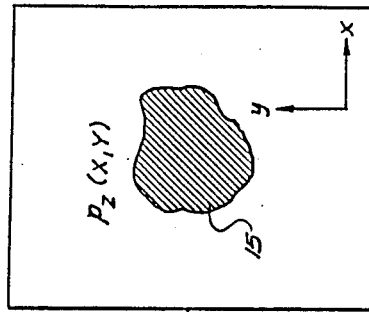
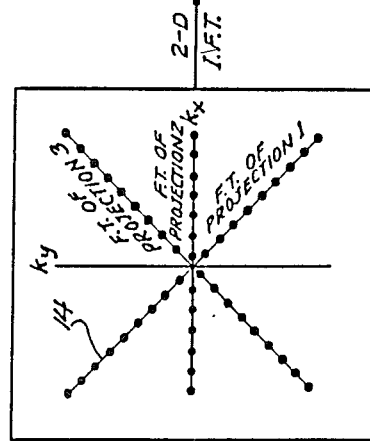
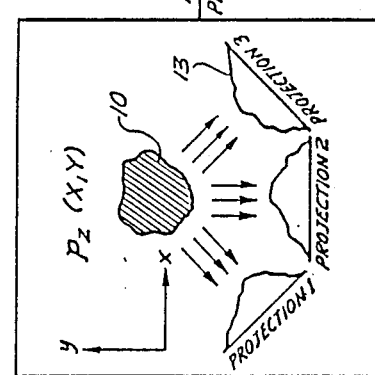
Fig. 3
Fig. 4

ULTRASOUND CHARACTERIZATION OF 3-DIMENSIONAL FLAWS

This application is a continuation of application Ser. No. 813,455, filed 12/26/85 now abandoned.

BACKGROUND OF THE INVENTION

This invention relates to a method of characterizing 3-dimensional flaws of general shape with ultrasound through the use of 2-dimensional tomographic image reconstructions.

By employing the current state-of-the-art ultrasound inspection techniques it is not yet feasible to determine the identity, shape, and orientation of a flaw if its size is smaller than the ultrasound beam diameter. For such a small flaw the composition and geometrical parameters are frequently estimated from their acoustic scattering pattern. In the three-dimensional inverse Born Approximation the back-scattered amplitude $A(\omega,\Omega)$ of plane acoustic wave incident on an isotropic homogenous flaw in an isotropic homogenous medium can be written in the form:

$$A(\omega, \Omega) = \omega^2 F(\{\mu\}) S(2\omega/v,\Omega) \qquad (1)$$

where $F\{\mu\}$ is a function of $\{\mu\}$ which denotes collectively the material parameters of the medium and the flaw, and $S(k, \Omega)$ is equal to the Fourier transform of the characteristic function $\rho(r)$ of the flaw in the direction $\Omega$ of the incident plane wave (see Rose, J. H. and Krumhansl, J. A., J. Appl. Phys. 50 (1979) 2951, 52). Here the characteristic function $\rho(r)$ specifies the flaw shape and is defined as equal to 1 inside the flaw and equal to 0 outside. With the substitution $k = \omega/v$ and rearranging, equation (1) can be written in the form $$S(k,\Omega) = 4A(kv/2,\Omega)/[k^2 v^2 F(\{\mu\})] \qquad (2)$$

In other words an ultrasonic inspection of a flaw at an angle $\Omega$ yields a line of Fourier components of the characteristic function $\rho(r)$ of the flaw, with the line oriented in the same direction $\Omega$ in the Fourier space and passing through the origin. This situation is illustrated in FIG. 1, where (x, y, z) denotes spatial coordinates in object space and ($k_x$, $k_y$, $k_z$) denotes spatial frequency coordinates in Fourier space. Therefore inspecting the flaw at all angles in a half space will yield all the Fourier components of $\rho(r)$, and from these Fourier components $\rho(r)$ can be reconstructed through 3-dimensional inverse Fourier transformation. The material parameters of the flaw can be determined from pitch catch measurements if desired (see Rose, J. H., and Richardson, J. M., J. Nondestr. Eval., 3 (1982) 45.)

Thus in order to characterize the flaw one has to inspect it from all $4\pi$ angles in 3 dimensions and perform an inverse 3-dimensional Fourier transform. Such a procedure involves a number of difficulties: (1) a large amount of data to take and process; (2) some angles may not be accessible to inspection; (3) complications associated with 3-dimensional image reconstructions, such as 3-dimensional interpolation, long computing time, etc. For these reasons the method is usually simplified and restricted to characterize symmetrically shaped flaws, which can be characterized by using only a small number of pulse echoes. This simplified procedure is known as the 1-dimensional inverse Born Approximation (see Rose, J. H. et al, "Inversion of Ultrasonic Scattering Data", Acoustic, Electromagnetic and Elastic Wave Scattering, V. V. Varadan and V. K. Varadan (Eds.), Pergamon, 1980). Though the procedure is simple, it cannot be applied to characterize flaws of more general shape.

SUMMARY OF THE INVENTION

An object of the invention is to develop a method to simplify the problem of characterizing 3-dimensional flaws of general shape with ultrasound by reducing it to a series of 2-dimensional tomographic image reconstructions. A standard computerized tomography (CT) algorithm is then used to get the 3-D shape.

Another object is to determine the size and shape of relatively small, non-symmetrically shaped flaws in an object by a simplified method that eliminates the drawbacks associated with 3-dimensional image reconstructions.

The improved method of characterizing 3-dimensional flaws of general shape with ultrasound is as follows. Pulse echo measurements are taken and return echo waveforms are acquired using broadband pulses of ultrasound that are incident on the flaw at many angles in a plane. The time Fourier transform of each pulse echo waveform gives the corresponding line of Fourier components, as mentioned above. Hence combining the inspections from many angles yields a plane of Fourier components of the characteristic function which specifies the shape of the flaw. From these Fourier components the 2-dimensional projection image is reconstructed. Then the plane on which the pulse echo measurements are made is rotated, and the foregoing steps are repeated; a plurality of 2-dimensional projection images are produced. The 3-dimensional flaw shape is reconstructed from the 2-dimensional projection images through a 3-D reconstruction process. If the flaw shape is not too irregular or fine details of the shape are not of interest, only a few projection images suffice to characterize the flaw.

Two implementations of the method are given. The first comprises deriving, from each line of Fourier components of the characteristic function, the spatial Fourier components of the flaw shape. A 1-dimensional inverse Fourier transform is then performed, line by line, to yield 1-dimensional projections of the 2-dimensional projection image. From the 1-dimensional projections the 2-dimensional projection image is reconstructed through a 2-D reconstruction.

The second implementation comprises angularly orienting and superimposing the lines of spatial Fourier components of the flaw shape. From the 2-D Fourier components the 2-dimensional projection image is reconstructed through a 2-D inverse Fourier transformation.

There are several advantages of the improved flaw characterization method. Among these are that it saves a lot of measurement time and computing time. In most cases, better image quality is achieved.

BRIEF DESCRIPTION OF THE DRAWINGS

FIG. 3 shows a 3-dimensional flaw and 2-dimensional and 1-dimensional projected images.

FIG. 4 illustrates 2-dimensional image reconstruction from projections.

DETAILED DESCRIPTION OF THE INVENTION

Figure 1A:
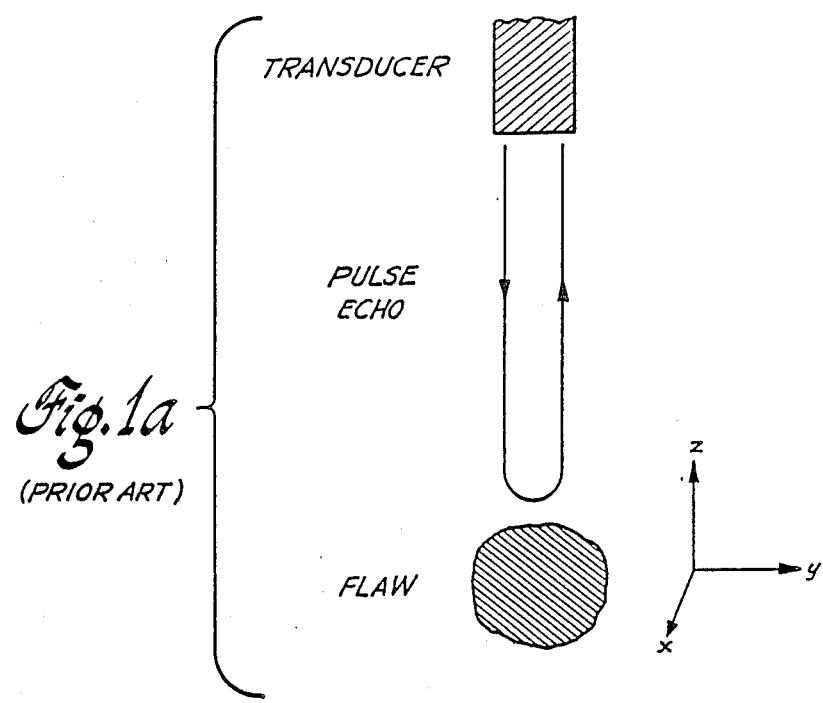
Figs. 1a and 1b (prior art) illustrate a pulse echo reflected from a flaw located at the origin, and the line of Fourier components calculated from it.
Figure 1B:
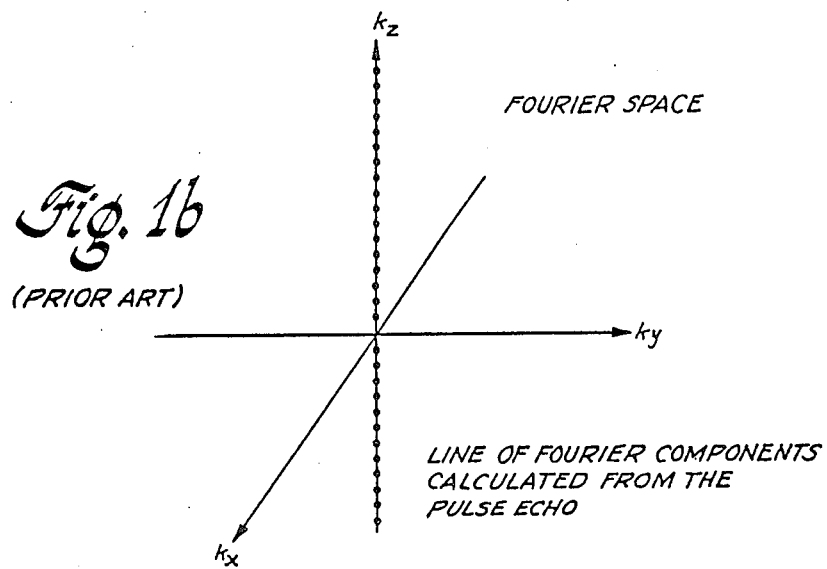
Figure 2A:
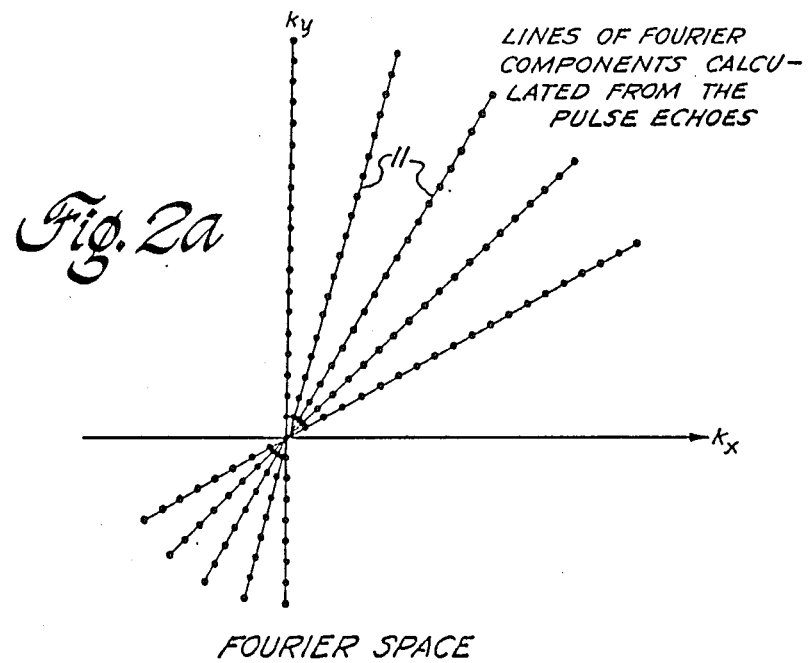
FIGS. 2a and 2b illustrate combining the pulse echo inspections from many angles to obtain many lines of Fourier components in Fourier space.
Figure 2B:
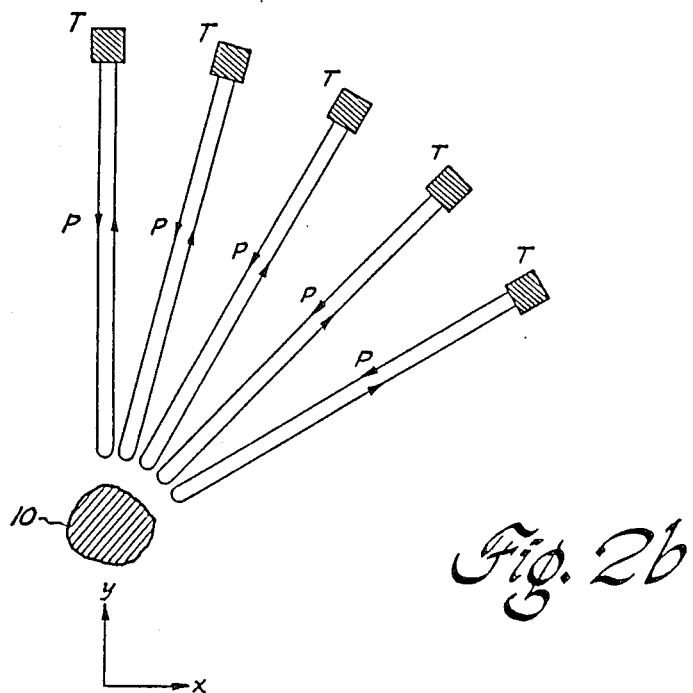

Referring to FIG. 2a and 2b, let inspections be performed at all $\pi$ angles in the x-y plane with the flaw 10 located at the origin. Only five transmitting and receiving transducers T and pulse echoes P are shown; the object containing the flaw is moved to scan over 180°. Broadband narrow pulses are used to achieve good high frequency resolution; a single pulse gives a line of Fourier components. The time Fourier transform of each pulse waveform, after dividing by the Fourier transform of the pulse shape of the transducer pule shape (deconvolution), and dividing by $k^2$, gives the corresponding line of Fourier components $S(k)$ of $\rho(r)$ in the Fourier space, as seen in Fig. 1b. Hence combining the inspections from all angles in the x-y plane, one obtains all lines of Fourier components 11 of $\rho(r)$ lying in the $k_x - k_y$ plane in the Fourier space.

The projection $p_z(x,y)$ of $\rho(r)$ in the z direction is defined by the equation:

$$p_z(x,y) = \int \rho(x,y,z) \, dz \qquad (3)$$

As illustrated in FIG. 3, the projection $p_z(x,y)$ or 2-dimensional projected image 12 represents the 2-dimensional shadow or silhouette of the 3-dimensional object viewed in the z direction. Now the Fourier components of $\rho(r)$ in the $k - k_y$ plane can be viewed as the 2-dimensional Fourier transform of the projection $\rho_z(x,y)$ in the z direction:

$$S(k_x,k_y,k_z)|_{k_z=0} = \int\int\int \rho(x,y,z) e^{2\pi i(k_x x + k_y y + k_z z)} \, dxdydz \,|_{k_z=0} \quad (4)$$
$$= \int dx e^{2\pi i k_x x} \int dy e^{2\pi i k_y y} \, p_z(x,y) \quad (5)$$

where $S(k_x, k_y, k_z)$ is the Fourier transform of the arbitrary 3-dimensional function $(x, y, z)$. Hence from the plane of Fourier components the projection $p_z(x, y)$ can be reconstructed through 2-dimensional inverse Fourier transformation. In a similar manner the 2-dimensional projection of $\rho(r)$ in any azimuthal direction can be reconstructed from the corresponding plane of Fourier components obtained from the echo waveforms. If there are missing Fourier components, they can be recovered by using the 2-dimensional version of the limited-angle reconstruction techniques discussed in the published paper by the inventor and V. PerezMendez, J. Opt. Soc. Am. 71 (1981) 582-592.

The waveforms should be normalized before attempting image reconstruction, because the magnitude of the pulse echo waveforms depends on such variables as the distance between the transducer and the flaw, the transmission coefficient at the object medium/water interface, and the solid angle subtended by the projection of the transducer area on the interface at the flaw, all of which usually change with the inspection angle. Normalization can be achieved by multiplying each deconvolved waveform by the reciprocal of the total area of the positive portion of the waveform or, equivalently, by the reciprocal of the value of the zeroth frequency component of the Fourier transform of the waveform.

The principle of the reconstruction of a 2-dimensional function $p_z(x,y)$, 15, from its 1-dimensional projections 13 is graphically illustrated in FIG. 4. By virtue of the projection theorem in computerized tomography, the Fourier transform of each 1-dimensional projection gives rise to a line of Fourier components 14 in the Fourier space. Therefore the entire 2-dimensional transform of $p_z(x,y)$ can be obtained by combining all of these lines of Fourier components, and $p_z(x,y)$ itself, 2-dimensional projection image 15, can be reconstructed by 2-dimensional inverse Fourier transformation.

The physical meaning of the 1-dimensional projection 13 can be seen in FIG. 3, where $P_z$ is the projection along the z direction and $P_y$ is the projection along the y direction. The function $p_{yz}(x)$ is defined which is the 1-dimensional projection or projected image of $\rho(x,y,z)$ onto the x axis; $P_{yz}(x)$ can be considered as the 1-dimensional projection of the 2-dimensional function $p_z(x,y)$ projected along the y direction onto the x axis. Given enough of these projections of $p_z(x,y)$ at all angles from o to $\pi$ in the x-y plane, the function $p_z(x,y)$ itself can be reconstructed uniquely. This is the well known result in computerized tomography. That only projections from o to $\pi$ instead of o to $2\pi$ are needed is due to the inversion symmetry of the projection operation, i.e. the projection at angle $\theta$ is the same as the projection at angle $\theta + \pi$. The reconstruction of $p_z(x,y)$ from its projections can be accomplished using object-space reconstruction algorithms such as filtered back projection, or it can proceed in Fourier space after taking the transform of the projections. The 1-dimensional function previously was used to derive a 1-dimensional projection, or, if there are many, to perform a 3-dimensional image reconstruction. This invention recognizes that the 1-dimensional functions in one plane can be used to perform a 2-dimensional image reconstruction.

It has been shown that $p_z(x,y)$ is the 2-dimensional image of the flaw shape projected along the z direction onto the x-y plane. The numerical value of the function is a measure of the thickness of the 3-dimensional object at each lateral position (x,y), and its shape represents the shadow or silhouette of the object viewed in the z direction. By rotating the plane on which the pulse echo measurements are made, one can obtain the 2-dimensional projection of $\rho(r)$ in other directions. If the shape of the flaw is not too irregular or if the fine details of the shape are not of interest, only a few of these projection images suffice to characterize the flaw. Only a few views of the flaw (less than 10) are needed to give an overall idea of its shape and size, and one needs only to inspect the flaw in the planes perpendicular to the views of interest. Of course, if enough of these 2-dimensional projections are measured $\rho(r)$ itself can be reconstructed completely.

There are several advantages in reducing the flaw characterization problem from reconstructing the 3-dimensional flaw shape to reconstructing the individual 2-dimensional projections of the flaw. First of all, it saves a lot of measurement time and computing time. As mentioned before, a small number of 2-dimensional projections usually suffice to give a fairly good estimate of the 3-dimensional flaw shape. Therefore only measurements in those planes are needed. In contrast, with 3-dimensional image reconstruction, inspections at all $4\pi$ steradians are always needed even if only a few views are actually of interest.

The second advantage of reducing the 3-dimensional image reconstruction to 2-dimensional image reconstruction is that in most cases better image quality can be achieved. It often happens that the flaw cannot be inspected in some angular range, and therefore the corresponding Fourier components at those angles are not available in reconstructing the flaw shape. The quality of the reconstructed image will be degraded if the reconstruction is performed in a 3-dimensional manner involving all the $4\pi$ Fourier components in the 3-dimensional Fourier space. In the reconstruction of a 2-dimensional projection of the flaw shape, however, only the Fourier components on the corresponding plane in the Fourier space are needed. Therefore it is possible to reconstruct some 2-dimensional projections without loss of information if, for these projection images, inspection is accessible at all the $2\pi$ angles in the corresponding inspection plane.

The third advantage is that if the flaw shape is convex, the reconstructions can be done much easier. In general, all the details in the pulse echo waveforms are needed in reconstructing the 2-dimensional projection images. But if the 3-dimensional flaw shape is convex, it can be shown that its 2-dimensional projection images are also convex. In this case these projection images can be reconstructed using only the shape of the pulse echo waveforms, their magnitude scale becomes unimportant. This simplified reconstruction procedure is especially advantageous in ultrasound inspection since the pulse echoes at different angles are not on the same scale, as mentioned before.

Even if the flaw shape is not convex and therefore its 2-dimensional projections may not be convex, using only the shape of the waveforms one can reconstruct the convex hull of the 2-dimensional projections. For a flaw not too irregular in shape, the convex hulls of its 2-dimensional projections are fairly good approximations for the projections themselves.

Figure 5:
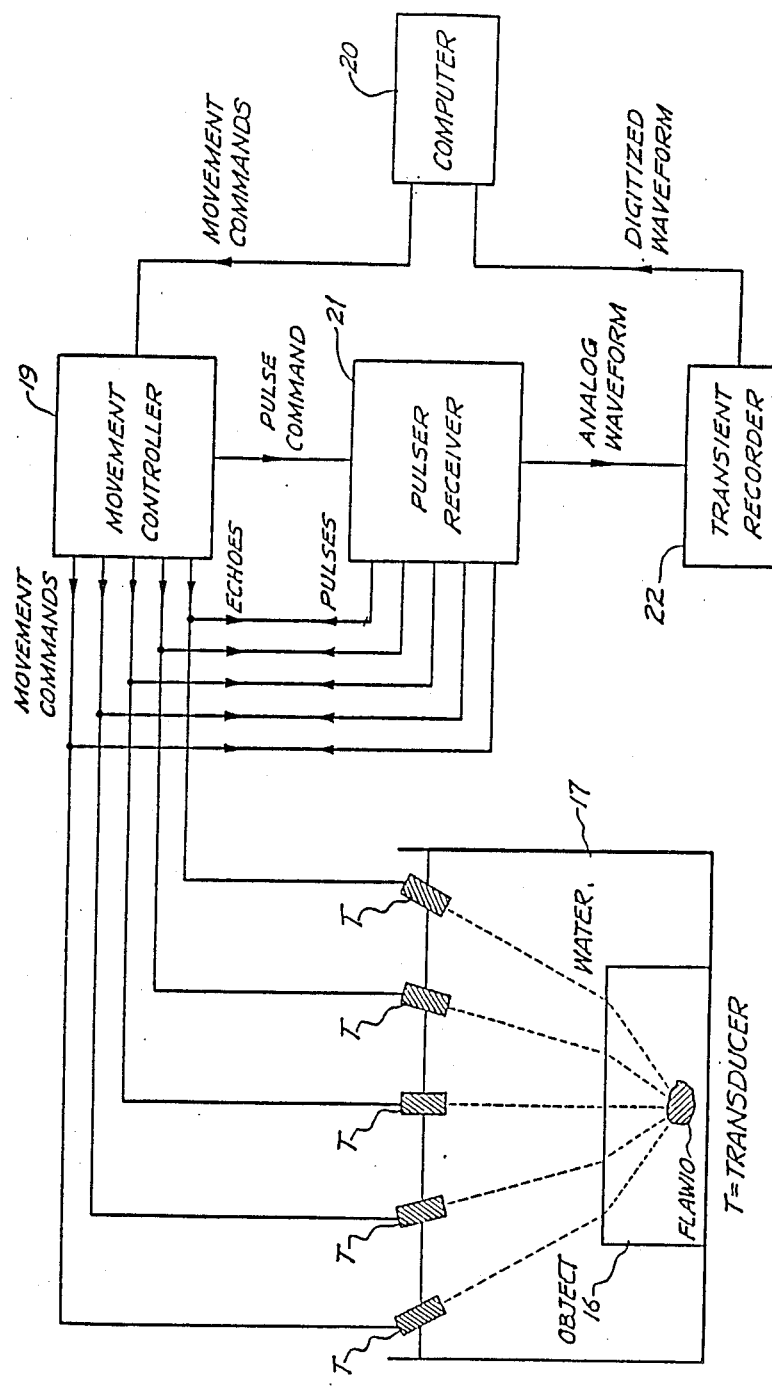
FIG. 5 shows one embodiment of an improved system to locate and inspect flaws by the method of this invention.

FIG. 5 shows a practical realization of the invention. An object 16 containing the flaw 10, typically a metallic workpiece having a void or inclusion, is inspected in a water bath 17. A number of matching unfocused transducers T (5 shown in the figure) are used to locate and inspect flaws. The transducers are positioned on a plane. The positions of the transducers in the plane can be adjusted to view the object at different polar angles by means of mechanical arms which can move the transducers around and tilt them at different angles. The azimuthal angle of the plane can also be varied by means of the same mechanical arms. The object 16 is rotated in order to inspect another plane. The movements of the mechanical arms are controlled by a movement controller 19 which is a microprocessor controlled by signals sent from the signal processing computer 20. After the transducers 18 are stabilized in each position and orientation the movement controller 19 sends a pulse command signal to start a pulser-receiver 21 whose pulses activate transducers T. The return echoes from the flaw 10 are detected by the transducers, sent to the pulser-receiver 21, and then to a transient recorder 22 which digitizes the analog waveforms for input to the signal processing computer 20. In the computer the digitized pulse echo waveforms are processed to yield the 2-dimensional projection images of the flaw shape.

Figure 6:
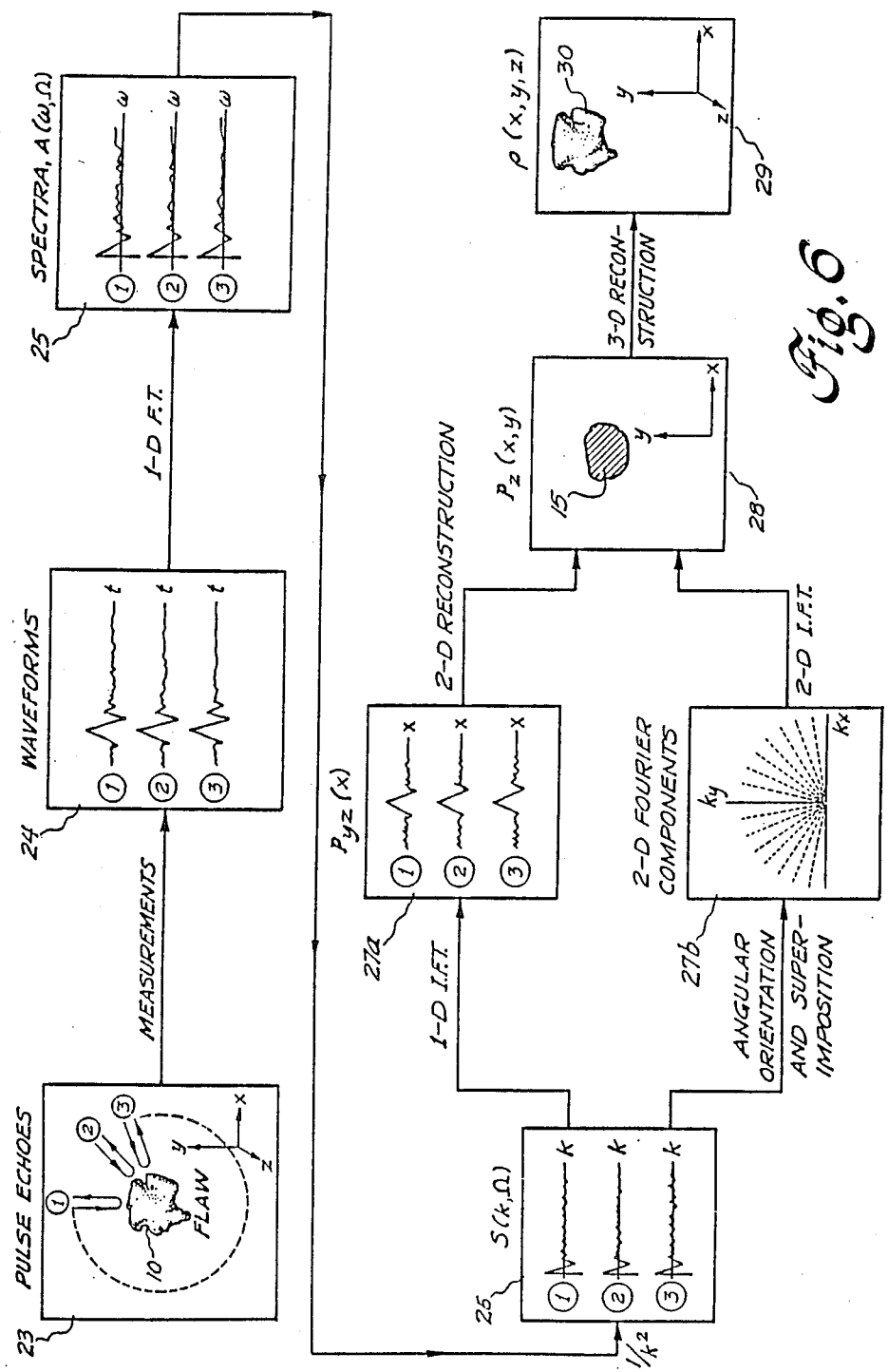
FIG. 6 shows graphically the complete procedure for reconstructing a 2-dimensional projection from pulse echoes.

The complete procedure and two alternative methods for reconstructing $p_z(x,y)$, the reconstructed 2-dimensional image, from the pulse echoes are graphically illustrated in FIG. 6. In the first block 23, pulse echo measurements using broadband incident pulses are taken at each incident angle in the x-y plane. Only three transducers an pulse echoes are used to explain the principle. The analog waveforms are illustrated in block 24. Each waveform is subjected to a 1-dimensional Fourier transform to yield the corresponding line of Fourier components in the Fourier space. Each line of Fourier components is normalized by multiplying each Fourier component by the reciprocal of the corresponding Fourier component of the waveform backscattered from the front surface of the medium, and by the reciprocal of the zeroth frequency Fourier component on the line. The purpose for the latter is to correct for the difference in the magnitude scale of the different pulse echos. The final result obtained (block 25) is the scattering amplitude $A(\omega,\Omega)$ in equation (1). This is the measured quantity. The factor $S(\omega,\Omega)$ is obtained from $A(\omega,\Omega)$ by dividing by $\omega^2$. Alternatively, referring to equation (2), $A(\omega,\Omega)$ is divided by $k^2$, a quantity proportional to the square of the angular frequency $(\omega)$ of the incident ultrasonic wave, to obtain the spatial Fourier components $S(k,\Omega)$ of the flaw shape as seen in block 26.

At this point there are two alternatives, diagramed in blocks 27a and 27b to obtain the 2-dimensional projection image 15 and $p_z(x,y)$. The first method processes one line at a time, or line by line, as is typically done in CT imaging. A 1-dimensional inverse Fourier transform is performed on every line of spatial Fourier components and gives the quantities $p_{yz}(x)$, the 1-dimensional projected image. From these 1-dimensional projections (see block 28) the quantity $p_z(x,y)$, the 2-dimensional projection image 15 of the flaw shape, is reconstructed, using object-space reconstruction algorithms.

The second method, illustrated by block 27b, comprises angularly orienting and superimposing the quantities $S(k,\Omega)$, the lines of spatial Fourier components, to obtain a plane of 2-D Fourier components. A 2-dimensional inverse Fourier transformation yields the 2-dimensional projection image 15 of the flaw shape. The final steps are to acquire a plurality of 2-dimensional projection images by rotating the plane on which pulse echo measurements are made and repeating the foregoing procedures. Referring to block 29, the 3-dimensional flaw shape 30 is reconstructed from these 2-dimensional projection images through a 3-dimensional reconstruction process.

Since the invention is capable of both reconstructing 3-dimensional flaws of general shape and yielding the material parameters of flaws of general shape, it has a wide range of applications in industrial ultrasound inspection. Among other things, it can be applied to identify flaws in the critical parts in nuclear reactors, aircraft engines, turbines, and other high-cost equipment.

Further explanation is given in "3-Dimensional Flaw Characterizations Through 2-Dimensional Image Reconstructions", Review of Progress in Nondestructive Evaluation, Vol. 5, Plenum Press, pp. 541–553. The same technical paper is published as TIS Report No. 85CRD199, Nov. 1985, General Electric Co., Corporate Research and Development, Schenectady, N.Y. 12345.

While the invention has been particularly shown and described with reference to preferred embodiments thereof, it will be understood by those skilled in the art that various changes in form and detail may be made without departing from the spirit and scope of the invention.

The invention claimed is:

1. A method which uses an improved Born approximation technique to determine with ultrasound a 3-dimensional flaw shape of flaws of general shape comprising the steps of :
    (a) taking pulse echo measurements and acquiring return echo waveforms using broadband pulses of ultrasound that are incident on a flaw in an object at a plurality of angles between 0 and $\pi$ in a chosen plane;
    (b) Fourier transforming said echo waveforms to yield lines of Fourier components of a characteristic function which is defined as equal to 1 inside the flaw and 0 outside the flaw;
    (c) dividing each line of Fourier components by a quantity proportional to incident ultrasound angular frequency squared to yield lines of spatial Fourier components of the flaw shape;
    (d) performing a 1-dimensional inverse Fourier transform on every such line of spatial Fourier components to yield a plurality of 1-dimensional projections;
    (e) performing a 2-dimensional reconstruction to reconstruct a 2-dimensional project image from said 1-dimensional projections;
    (f) rotating the plane on which said pulse echo measurements are made and repeating steps (a) to (e) to produce a plurality of said 2-dimensional projection images; and
    (g) reconstructing the 3-dimensional flaw shape from said 2-dimensional projection images through a 3-dimensional tomographic reconstruction process.

2. The method of claim 1 wherein there are less than ten of said 2-dimensional projection images from which the 3-dimensional flaw shape is reconstructed.

3. The method which uses an improved Born approximation technique to determine with ultrasound a 3-dimensional flaw shape of flaws of general shape comprising the steps of:
    (a) taking pulse echo measurements and acquiring return echo waveforms using broadband pulses of ultrasound that are incident on a flaw in an object at a plurality of angles between 0 and $\pi$ in a chosen plane;
    (b) Fourier transforming said echo waveforms to yield lines of Fourier components of a characteristic function which is defined as equal to 1 inside the flaw and 0 outside the flaw;
    (c) dividing each line of Fourier components by a quantity proportional to incident ultrasound angular frequency squared to yield lines of spatial Fourier components of the flaw shape;
    (d) angularly orienting said lines of spatial Fourier components to result in a plane of Fourier components;
    (e) performing a 2-dimensional inverse Fourier transformation to yield a 2-dimensional projection image of the flaw shape;
    (f) rotating the plane on which said pulse echo measurements are made and repeating steps (a) to (e) to produce a plurality of said 2-dimensional projection images; and
    (g) reconstructing the 3-dimensional flaw shape from said 2-dimensional projection images through a 3-dimensional tomographic reconstruction process.

4. The method of claim 3 wherein there are less than ten of said 2-dimensional projection images from which the 3-dimensional flaw shape is reconstructed.

* * * * *